(12) United States Patent
Bolisetty et al.

(10) Patent No.: US 12,290,091 B2
(45) Date of Patent: May 6, 2025

(54) COMPOSITE MATERIALS COMPRISING AMYLOID FIBRILS AND NANOPARTICULATE NUTRITIONAL MINERALS

(71) Applicant: ETH Zurich, Zürich (CH)

(72) Inventors: Sreenath Bolisetty, Zürich (CH); Michael Zimmermann, Rapperswil (CH); Yi Shen, Birmingham (GB); Raffaele Mezzenga, Volketswil (CH)

(73) Assignee: ETH Zurich, Zürich (CH)

( * ) Notice: Subject to any disclaimer, the term of this patent is extended or adjusted under 35 U.S.C. 154(b) by 488 days.

(21) Appl. No.: 17/827,904

(22) Filed: May 30, 2022

(65) Prior Publication Data

US 2022/0287348 A1    Sep. 15, 2022

Related U.S. Application Data

(63) Continuation-in-part of application No. 16/492,316, filed as application No. PCT/EP2018/056023 on Mar. 12, 2018, now Pat. No. 11,344,599.

(30) Foreign Application Priority Data

Mar. 13, 2017 (EP) .................... 17160624

(51) Int. Cl.
A23L 33/185 (2016.01)
A23L 33/16 (2016.01)
B82Y 5/00 (2011.01)

(52) U.S. Cl.
CPC ............ *A23L 33/185* (2016.08); *A23L 33/16* (2016.08); *B82Y 5/00* (2013.01)

(58) Field of Classification Search
CPC ...... A23L 33/185; A23L 33/16; A23L 33/105; B82Y 5/00; B82Y 30/00
See application file for complete search history.

(56) References Cited

U.S. PATENT DOCUMENTS

2006/0030619 A1 * 2/2006 Liu .................. A61K 31/195
514/566

FOREIGN PATENT DOCUMENTS

| WO | 2013010966 A1 | 1/2013 |
| WO | 2014124546 A1 | 8/2014 |
| WO | 2018166947 A1 | 9/2018 |

OTHER PUBLICATIONS

Acosta, "Bioavailability of nanoparticles in nutrient and nutraceutical delivery", Elsevier, Current Opinion in Colloid & Interface Science, 14 (2009) 3-15.

(Continued)

*Primary Examiner* — Hong T Yoo
(74) *Attorney, Agent, or Firm* — Renner, Otto, Boisselle & Sklar, LLP

(57) ABSTRACT

The use of amyloid fibrils for providing nutritional minerals to the human body, particularly as a component in a food product, a dietary supplement or in a pharmaceutical product. Compositions including composite materials of amyloid fibrils and nutritional minerals. The use of such composite materials in the treatment of diseases and disorders and to the fortification of food and dietary supplements with nutritional minerals.

14 Claims, 1 Drawing Sheet

(56) References Cited

OTHER PUBLICATIONS

Figure 1:
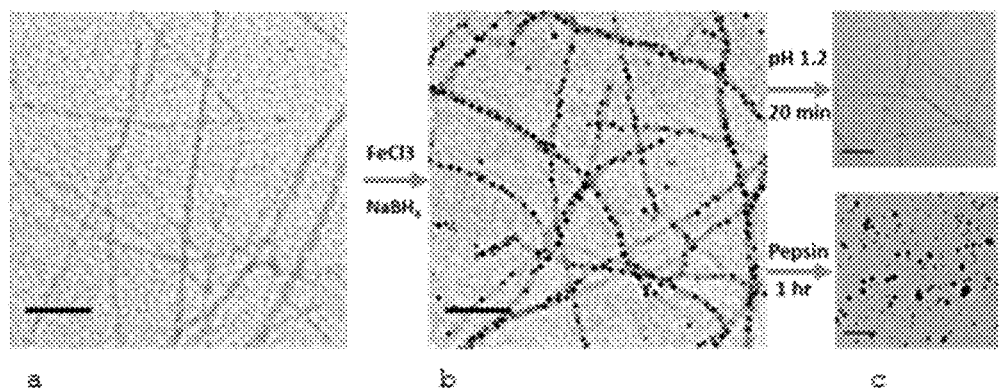

Bolisetty et al., "Magnetic-Responsive Hybrids of Fe304 Nanoparticles with β-Lactoglobulin Amyloid Fibrils and Nanoclusters", 2013 American Chemical Society, Jun. 10, 2013, vol. 7, No. 7, 6146-6155.

Ghani et al., "Unveiling Amyloid-β1-42 Interaction with Zinc in Water and Mixed Hexafluoroisopropanol Solution in Alzheimer's Disease", Springer Science+Business Media New York 2017, Accepted: Dec. 16, 2016 / Published online: Feb. 2, 2017, Int J Pept Res Ther (2017) 23:393-407.

Hilty et al., "Iron from nanocompounds containing iron and zinc is highly bioavailable in rats without tissue accumulation", published online Apr. 25, 2010, vol. 5, May 2010, 374-380.

Huber, "Synthesis, Properties, and Applications of Iron Nanoparticles", small 2005, 1, No. 5, 482-501.

Hurrell, "Forging Effective Strategies to Combat Iron Deficiency", The Journal of Nutrition, 132: 806S-812S, 2002.

Mittal et al., "Iron binding to caseins in the presence of orthophosphate", Elsevier, Food Chemistry 190 (2016) 128-134.

Rohner et al., "Synthesis, Characterization, and Bioavailability in Rats of Ferric Phosphate Nanoparticles", The Journal of Nutrition, Nutrient Physiology, Metabolism, and Nutrient-Nutrient Interactions, 137: 614-619, 2007.

Viles, "Metal ions and amyloid fiber formation in neurodegenerative diseases. Copper, zinc and iron in Alzheimer's, Parkinson's and prion diseases", Elsevier, Coordination Chemistry Reviews 256 (2012) 2271-2284.

Allen et al., "Guidelines on food fortification with micronutrients", World Health Organization, 2006.

International Search Report and Written Opinion for corresponding International Application No. PCT/EP2018/056023 dated Apr. 30, 2018.

Amar-Yuli et al., "Templating effects of lyotropic liquid crystals in the encapsulation of amyloid fibrils and their stimuli-responsive magnetic behavior", Soft Matter, 7, 3348-3357, 2011.

Jung et al. "Structure of Heat-Induced β-Lactoglobulin Aggregates and their Complexes with Sodium-Dodecyl Sulfate", Biomacromolecules, 9, 2477-2486, Aug. 13, 2008.

Allowed claims of related U.S. Appl. No. 16/492,316, filed Sep. 9, 2019.

* cited by examiner

COMPOSITE MATERIALS COMPRISING AMYLOID FIBRILS AND NANOPARTICULATE NUTRITIONAL MINERALS

This application is a Continuation in Part of U.S. application Ser. No. 16/492,316 filed Sep. 9, 2019, which is a national phase of International Application No. PCT/EP2018/056023 filed Mar. 12, 2018, which claims priority to European Application No. EP 17160624.7 filed Mar. 13, 2017, the disclosures of which are hereby incorporated by reference in their entireties.

The present invention relates to the use of amyloid fibrils for providing nutritional minerals to the human body, particularly as a component in a food product, a dietary supplement or in a pharmaceutical product. The invention further provides for new compositions comprising composite materials of amyloid fibrils and nutritional minerals. The invention further relates to the use of such composite materials in the treatment of diseases and disorders and to the fortification of food and dietary supplements with nutritional minerals.

Composite materials of Fe3O4 and beta-lactoglobulin amyloid fibrils (fibBLG) are a known; their synthesis and magnetic behaviour is described in Bolisetty et al (ACS Nano, 2013, 7, 6146). Also, composite materials of Gold and fibBLG are a known; their synthesis and shaped articles comprising them are described in Li et al (WO2014/124546). These documents are silent about any use in the context of oral administration or feeding to humans.

It is well known that a balanced diet is essential in maintaining good health. Hence, the nutritional value of foods is an important aspect that should be considered especially with respect to metal intake. Food fortification is a well-established strategy to address this issue. Particularly iron as a nutritional metal is a challenge for food fortification. Hurrell et al (Heal. Promot. 2002, 1, 806) identify the challenges of iron fortification, namely (1) finding an iron compound that is adequately absorbed but causes no sensory changes to the food vehicle; and (2) overcoming the inhibitory effect on iron absorption of dietary components. Further, Huber et al (Small, 2005, 1, 482) discusses applications of iron nanoparticles, particularly pointing out the difficulties in handling, due to its extreme reactivity. Typically, iron compounds used for oral supplementation are limited by low absorption of the iron (resulting in poor efficacy) and/or show gastric irritation (resulting in poor compliance). Also, Grage et al (WO2013/010966) discuss that fortification of food with micronutrients such as iron is not a straightforward procedure. They propose encapsulates embedded in a polysaccharide phase, said encapsulate comprising gelled proteins aggregates of 1-5000 micron and containing a micronutrient. Although suitable, such encapsulates are difficult to manufacture and handle. Further, they are limited in the choice of micronutrient and in their applications.

Thus, it is an object of the present invention to mitigate at least some of these drawbacks of the state of the art. In particular, it is an aim of the present invention to provide for a versatile platform technology in food fortification.

These objectives are achieved by the use of amyloid fibrils as defined in claim 1, composite materials as defined in claim 2 and compositions as defined in claim 10. Further aspects of the invention are disclosed in the specification and independent claims, preferred embodiments are disclosed in the specification and the dependent claims.

The present invention will be described in more detail below, referring to the first, the second and the third aspect of the invention. The first aspect is directed to new uses of amyloid fibrils and composite materials comprising amyloid fibrils including their manufacturing. The second aspect is directed to composite materials comprising amyloid fibrils and nutritional minerals in food products, dietary supplements and pharmaceutical compositions. The third aspect is directed to pharmaceutical uses of such composite materials.

Unless otherwise stated, the following definitions shall apply in this specification:

It is understood that the various embodiments, preferences and ranges as provided/disclosed in this specification may be combined at will. Further, depending of the specific embodiment, selected definitions, embodiments or ranges may not apply.

The terms "a," "an," "the" and similar terms used in the context of the present invention (especially in the context of the claims) are to be construed to cover both the singular and plural unless otherwise indicated herein or clearly contradicted by the context. The terms "including", "containing" and "comprising" are used herein in their open, non-limiting sense.

As used herein, the term "Food Fortification" refers to the practice of deliberately increasing the content of an essential micronutrient, particularly nutritional minerals in a food product irrespective of whether these micronutrients were originally in the food before processing or not. By doing so, the nutritional quality of the food is improved and a health benefit is typically provided for.

As used herein the term "minerals" is used in the context of nutrition, i.e. "minerals essential for mammals, particularly humans". In the context of nutrition, a mineral is a compound comprising one or more chemical elements required as an essential nutrient by the organism to perform functions necessary for life. The term minerals shall include "major minerals" and "trace minerals", the latter also referred to as "trace elements". The term major minerals particularly includes compounds comprising the chemical elements calcium, phosphorus, potassium, sodium, and magnesium. The term trace minerals particularly includes compounds comprising the chemical elements iron, cobalt, copper, zinc, manganese, molybdenum, iodine, and selenium. In the context of this invention "major minerals" and "trace minerals" are also collectively termed "nutritional minerals".

The present invention will be better understood by reference to the figures.

FIG. 1 shows TEM images of the materials described herein.

a. Amyloid fibrils were produced by heating the 2 wt % of purified beta-lactoglobulin (BLG) protein monomer (pH 2) at 90° C. for 5 h. (scale bar is 100 nm)

b. Iron nanoparticles were synthesized onto amyloid fibrils by in situ chemical reduction of $FeCl_3.6H_2O$ to obtain iron-BLG fibrils (i.e the composite materials comprising amyloid fibrils and nanoparticulate mineral compounds located on the surface of said amyloid fibrils). 0.45 wt % of amyloid fibrils was mixed with 0.015M $FeCl_3.6H_2O$ salt solutions. Fe III ions binding to amyloid fibrils were chemically reduced by $NaBH_4$. (scale bar is 100 nm)

c. In-vitro acidic/enzymatic digestion of iron-BLG fibrils. By decreasing the pH value to 1.2 at 37° C. for 20 min, the iron particles are readily dissolved and only fibrils are detected (top image, scale bar is 200 nm). Fibrils are digested by pepsin at 37° C. for 1 hour resulting in iron nanoparticles aggregation. (bottom image, scale bar is 200 nm).

Figure 2:
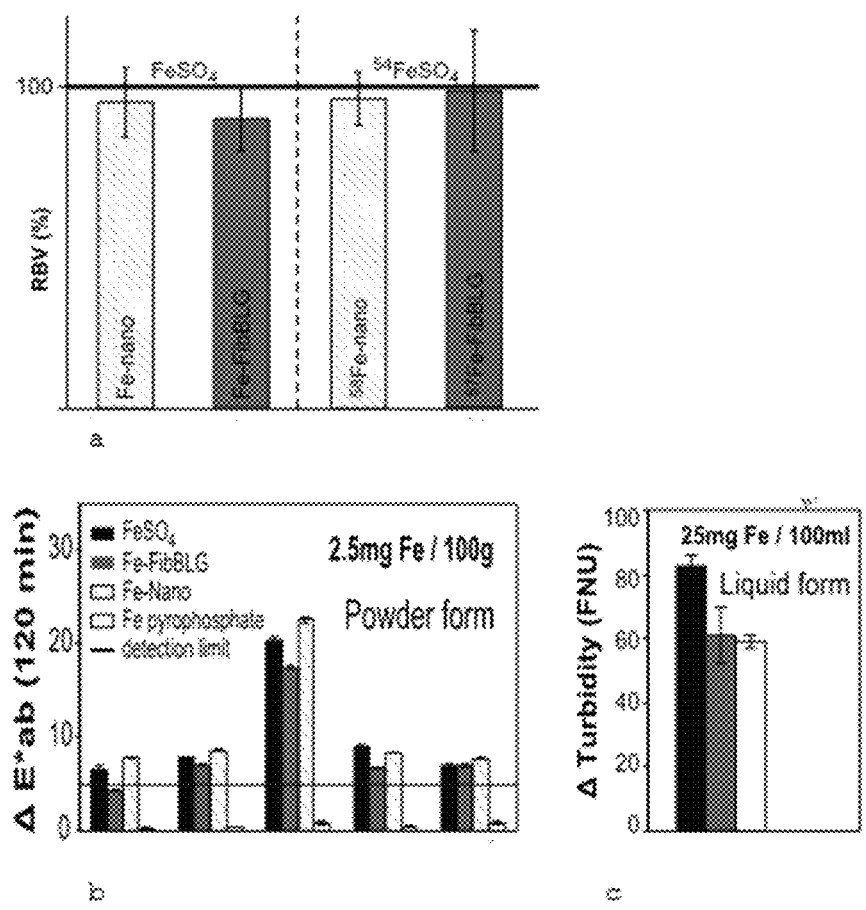

FIG. 2 shows in vivo study results and sensory performance.

a. Relative bioavailability (RBV %) with confidence intervals (CI) for powder (left) and liquid compounds (right) against $FeSO_4$ (100%). Light-grey: Fe-Nano, Dark-Grey: iron-BLG fibrils. No statistical difference in RBV was detected between compounds or when compared to $FeSO_4$ in both powder and liquid form (p>0.05).

b. Color change of iron-containing compounds in powder form in selected food matrices at 2.5 mg iron/100 g food matrix. y-axis: Absolute color change, $\Delta E^*_{ab} \pm sd$, of 2 replicates is given at 120 min against the non-fortified matrix. x-axis from left to right: chocolate milk, raspberry yoghurt milk, banana milk, cereal based infant formula, fruit-based infant food.

Black: $FeSO_4$; light-grey: Fe-Nano, dark-grey: iron-BLG fibrils. The detection limit is indicated; iron-BLG fibrils outperform Fe-Nano and $FeSO_4$.

c. Turbidity of iron-containing compounds in liquid form, compared in fish source at 25 mg iron/100 ml fish sauce. Δ Turbidity is relative to Formazin standard solution (FNU) and against the non-fortified fish sauce. Black: $FeSO_4$; white: Fe pyrophosphate, dark-grey: iron-BLG fibrils. Iron nano compounds could not be tested for turbidity as they rapidly sediment in liquids.

In more general terms, in a first aspect, the invention provides for the use of amyloid fibrils for providing nutritional minerals to the human body.

Advantageously, these amyloid fibrils are present in the form of a composite material, said composite material comprising (a) amyloid fibrils and (b) one or more nanoparticulate minerals located on the surface of said amyloid fibrils. Advantageously, these amyloid fibrils are a component in a food product, a dietary supplement or in a pharmaceutical product.

This aspect of the invention shall be explained in further detail below:

Amyloid fibrils (a): The term "amyloid fibrils" is generally known in the field to describe a specific type of protein aggregates and particularly describes fibrils made by proteins or peptides prevalently found in beta-sheet secondary structure. Accordingly, the term amyloid fibrils excludes native proteins. Amyloid fibrils made of pathological proteins are known for their association with neurodegenerative disorders, see e.g. Viles et al (Coordination chemistry review, 256, 2012, 2271) and Ghani et al (Int J Pept Res Ther 23, 2017. 393).

It was surprisingly found that amyloid fibrils are efficient carriers for nutritional minerals, particularly for iron fortification and/or zinc fortification. Particularly suitable are amyloid fibrils from β-lactoglobulin, an inexpensive milk protein with natural reducing effects, which proves to act as an anti-oxidizing nanocarrier and colloidal stabilizer for nanparticulate minerals, such as nanoparticulate iron compounds.

In case of iron, the resulting composite material forms a stable protein-iron colloidal dispersion undergoing rapid dissolution and release of iron ions during acidic and enzymatic in-vitro digestion. Importantly, this composite shows high in-vivo iron bioavailability, equivalent to ferrous sulfate in hemoglobin repletion and stable isotope studies in rats, but with reduced organoleptic changes in foods, as further detailed in the examples provided below. Feeding the rats with these composite materials did not result in abnormal iron accumulation in any organs, or changes in whole blood glutathione concentrations, inferring their primary safety. Therefore, these nanoparticulate iron—amyloid fibril—composites emerge as highly effective delivery systems for iron in both solid and liquid matrices.

Advantageously, the amyloid fibrils have high aspect ratio, preferably with ≤10 nm in diameter and ≥1 μm in length.

Advantageously, the amyloid fibrils have a highly charged surface. The term highly charged surfaces is generally known in the field and particularly describes surfaces showing electrophoretic mobility of the order 2 μm·cm/V·s at pH 4. Accordingly, amyloid fibrils having an electrophoretic mobility of the order 1-4 μm·cm/V·s at pH 4 are preferred.

Advantageously, the amyloid fibrils are obtained from globular proteins, advantageously food grade globular proteins. Suitably, globular proteins are selected from the group consisting of beta-lactoglobulin (BLG), whey, lysozyme, Bovine serum albumin, soy proteins, and ovalbumin, preferably beta-lactoglobulin. In a further embodiment, globular proteins are selected from oat.

Nanoparticulate minerals (b): This term defines both, particle size and chemical composition of the particles. As the term "nano" implies, particles of 5-100 nm size (as determined by microscopy) are particularly useful in the context of this invention. The particle size may vary, depending on the mineral. As an exemplary embodiment, for iron, a preferred range of the particles is 5-20 nm. As a further exemplary embodiment, for zinc or calcium, a preferred range of the particles is 20-100 nm. Suitable particle sizes may be determined by the skilled person in routine experiments.

Broadly speaking, any known mineral may be used; preferred are nutritional minerals as defined above. As used herein, the term minerals shall particularly include compounds selected from the group consisting of salts, oxides and hydroxides.

Nutritional minerals: The term is known in the field and discussed above. Accordingly, the term includes the five major minerals in the human body (calcium, phosphorus, potassium, sodium, and magnesium containing minerals) and the trace minerals (iron, copper, zinc, manganese, molybdenum, iodine, and selenium containing minerals), particularly Fe, Ca, Mg, and Zn containing minerals; and very particularly Fe containing minerals.

Nanoparticulate iron minerals: Iron being required e.g. for haemoglobin and for the treatment of various diseases as outlined herein. The term includes oxides, hydroxides and salts of iron. The term includes stoichiometric and non-stoichiometric compounds. Iron (II) being preferred. Iron (II) compounds relates to chemical entities with iron in the oxidation state +2. As it is known, iron is absorbed in the human intestine only as Fe+2, and is therefore more bioavailable in oxidation states +2. In accordance with this invention iron (II) compounds contain at least 50 mol-% iron in oxidation state +2, preferably at least 66 mol-%, particularly preferably at least 75 mol % (each in respect to the total amount of iron). Typically, iron (II) compounds are present as a salt, oxide or hydroxide and combinations thereof. Consequently, the following exemplary compounds are included: Fe (II) oxides, Fe (II) hydroxides, Fe(II) salts. These nanoparticulate iron (II) compounds may comprise a metallic Fe core, thereby forming nanoparticles of the core-shell type.

Nanoparticulate calcium minerals: Calcium is essential to humans as an important constituent of bones and teeth, and of nerve function. Calcium containing nanoparticles can be attached on amyloid fibrils (particularly BLG fibrils) as well, forming a stable dispersion and potentially deliver calcium in a more bioavailable way with organic compound. As exemplary compounds Calcium carbonate calcium phosphate, calcium pyrophosphate, calcium citrate, are mentioned, particularly suitable is Calcium carbonate.

Nanoparticulate magnesium minerals: Magnesium is essential for humans as it is required for more than 300 biochemical reactions in the body that maintain normal nerve, immune system, heart, bone and muscle function. Magnesium containing nanoparticles can be generated in situ along the amyloid fibrils (particularly BLG fibrils) forming stable dispersions, allow fortification in liquid and potentially increase the bioavailability. As exemplary compounds, magnesium oxide and magnesium sulfate are mentioned.

Nanoparticulate zinc minerals: Zinc deficiency is a global health problem that causes growth retardation and poor immune function. Zinc containing nanoparticles can be nucleated in situ on the surface of amyloid fibrils (particularly BLG fibrils). The resulting composite forms stable dispersions, potentially increases the bioavailability. Further, it provides for an antibacterial effect to thereby extend the fortified foods' shelf life. As exemplary compounds, zinc oxide and zinc sulfate are mentioned.

Composite material: According to the invention, constituents (a) and (b) are in intimate contact. The individual constituents remain separate and distinct within the finished structure, the nanoparticulate mineral (b) being present on the surface of the amyloid fibrils (a). Without being bound to theory, it is believed that this is ensured by the manufacturing process and involves adsorption of the nanoparticles (b) on the fibrils (a) due to different surface charge. The composite material may be described as either of amyloid fibrils, worm-like or spherical nanoclusters (a), in each case being decorated with nanoparticulate material (b). The material exhibits properties of both, amyloid fibrils and nanoparticulate mineral, and is therefore also termed hybrid material. FIG. 1 shows the structure of the composite material. As can be seen, nanoparticles (b) are predominantly located on the surface of the amyloid fibrils (a), such as at least 90% of the nanoparticles, preferably at least 95% of the nanoparticles are located on the surface (in respect to the total amount of nanoparticles present in the composite). Particularly preferably, all nanoparticles (b) are present on the surface of the amyloid fibrils (a).

It was surprisingly found that constituents (a) and (b) of the composite material synergistically interact when administered. The ratio of both constituents may vary over a broad range, depending inter alia on the specific materials and the intended use. Particularly good results are obtained, in case the ratio (a)/(b) is in the range of 20/1 to 1/1 (w/w), such as 5/1.

The composite material may be present in various forms. In one embodiment, the composite material is present as a dry material, preferably-freeze dried material. In one alternative embodiment, the composite material is present as a gel, preferably as an aqueous gel comprising NaCl as an additional component. In one alternative embodiment, the composite material is present as an aqueous solution, preferably having a pH of 2.7-4 or having a pH of 6-10.

A particularly suitable composite material is obtained when combining fibBLG (component a) and nanoparticulate iron minerals (compound b). XPS analysis of this composite material revealed a complex structure of component (b), showing the presence of Fe(II) oxide and Fe(III) oxi-hydroxide formed around the iron cores, with the residual Fe(II)—$Cl_2$ and Fe(III)—$Cl_3$ on the nanoparticles surface. As shown in the experiments provided below, these composite materials show the same bioavailability as $FeSO_4$ but with improved sensory performance; further they are colloidally more stable than standard forms of nanosized iron. Without being bound to theory, it is believed that BLG fibrils stabilize iron in oxidation state (II), which is the more bioavailable oxidation state. Further, it is believed that the BLG fibrils prevent iron from colloidal aggregation. Still further, it is believed that BLG fibrils also protect iron against dietary inhibitors, such as phytate, polyphenols and calcium. These beneficial effects make composite materials comprising (a) BLG fibrils and (b) nano-particulate iron minerals located on the surface of said amyloid fibrils a particularly promising carrier and delivery system for nanosized iron, therefore useful for iron fortification of compositions as described below.

A further particularly suitable composite material is obtained when combining amyloid fibrils obtained from oat (component a) and nanoparticulate iron minerals (compound b). XPS analysis of this composite material revealed a complex structure of component (b), showing the presence of Fe(II) oxide and Fe(III) oxi-hydroxide formed around the iron cores, with the residual Fe(II)—$Cl_2$ and Fe(III)—$Cl_3$ on the nanoparticles surface. It was found these composite materials show the same bioavailability as $FeSO_4$ but with improved sensory performance; further they are colloidally more stable than standard forms of nanosized iron. Without being bound to theory, it is believed that fibrils obtained from oat stabilize iron in oxidation state (II), which is the more bioavailable oxidation state. Further, it is believed that the such fibrils prevent iron from colloidal aggregation. Still further, it is believed that such fibrils also protect iron against dietary inhibitors, such as phytate, polyphenols and calcium. These beneficial effects make composite materials comprising (a) BLG fibrils and (b) nano-particulate iron minerals located on the surface of said amyloid fibrils a particularly promising carrier and delivery system for nanosized iron, therefore useful for iron fortification of compositions as described below.

Compositions: As outlined above, the amyloid fibrils, or composite materials respectively, are not directly administered/supplied to a human being. Rather, they may be a component of a wide variety of compositions, including food products, dietary supplements and pharmaceutical compositions. Accordingly, the invention also provides for the use of amyloid fibrils/composite materials as described herein in the manufacturing of a food product, dietary supplement and pharmaceutical composition.

Manufacturing: The composite materials described herein are simple in manufacturing, using starting materials readily available. The ratio of component (a) and (b) can be altered by varying the initial weight fractions of the two starting materials. Depending on the nature of compound (b), various approaches for manufacturing the composite material are available. Accordingly, the manufacturing is known per se but not yet applied to the specific starting materials required in the context of the present invention.

The invention thus provides for a method for manufacturing a composite material as described herein, The manufacturing may take place at room temperature, or at slightly elevated temperatures.

Typically, an aqueous suspension of amyloid fibrils is provided first. The synthesis of amyloid fibrils is a known technology. Suitable is in particular protein hydrolysis followed by β-sheets driven fibrillation, as described e.g. in Jung et al. (Biomacromolecules. 2008, 9, 2477-2486). The self-assembly process is facile and controllable. Typical process parameters include incubating protein solution (e.g. 2 wt. % β-lactoglobulin) for a prolonged period of time (e.g.

5 h) under acidic conditions (e.g. pH~2), low ionic strength (e.g. I≤20 mM), high temperature (e.g. T~90° C.). Suitable proteins are food-grade proteins, which are structural stable, wide accessible and inexpensive. Such proteins allow preparation of amyloid fibrils, such as β-lactoglobulin. Suitable proteins may be selected from the group consisting of β-lactoglobulin, lysozyme, ovalbumin, and serum albumins.

For certain applications the obtained composite material may be directly used. However, the obtained composite material is typically filtered through a support material for further use, particularly for manufacturing a composition as defined above.

In one embodiment, the manufacturing of composite material as described herein comprises the steps of (i) preparation of amyloid fibrils in an aqueous medium, preferably by self-assembly at low pH and low ionic strength; and (ii) combining these amyloid fibrils with a solution comprising metal ions as defined above followed by a reducing agent (preferably NaBH4) to thereby obtain the composite material; and (iii) optionally further treatment. This manufacturing involves the in-situ synthesis of nanoparticulate minerals in step (ii) by providing a suitable solution comprising the metal ions (cations) and optionally the anions required to obtain component (b).

In one alternative embodiment the manufacturing of composite material as described herein comprises the steps of (i) preparation of amyloid fibrils in an aqueous medium, preferably by self-assembly at low pH and low ionic strength; and (ii) combining these amyloid fibrils with a suspension of pre-fabricated nanoparticulate minerals to thereby obtain the composite material; and (iii) optionally further treatment. This manufacturing involves the ex-situ synthesis of nanoparticulate minerals and is described e.g. in Bolisetty et al (cited above).

Use: As outlined above, the composite materials are useful as outlined herein, particularly as component/additive to food products, to dietary supplements and to pharmaceuticals.

Accordingly, the invention also provides for the use of amyloid fibrils as described herein for food fortification and for use of composite materials as described herein for food fortification.

Accordingly, the invention also provides for a method for providing minerals, particularly nutritional minerals, to the human body, said method comprising the step of administering/feeding amyloid fibrils or composite materials (both as described herein) as a component in a composition selected from the group consisting of food products, dietary supplements and pharmaceutical products.

In a second aspect, the invention relates to compositions comprising the composite materials described herein, said compositions being selected from the group consisting of food products, dietary supplements and pharmaceutical compositions.

This aspect of the invention shall be explained in further detail below.

Food Products: The term food product is known in the field and describes material, usually of plant or animal origin, that contains essential nutrients (such as carbohydrates, fats, proteins, vitamins, or minerals) and is ingested and assimilated by an organism to produce energy, allow for growth, and maintain life. Accordingly the term includes drinks and snack products.

Drinks particularly include flavoured milk products and yoghurt products. Snack products particularly include cereal based products and fruit based products. Liquid sauce formulations particularly include fish sauce and soy sauce.

Powder formulations particularly include powdered soup, powdered vegetable sauces, powdered fruit juice and milk powders.

The amount of composite material (b) (as described herein, 1$^{st}$ aspect of the invention) may vary over a broad range and typically amounts to 1-10 mg nutritional mineral (such as nanoparticular iron mineral) per 100 g food product, preferably 2-3 mg nutritional mineral (such as nanoparticular iron mineral) per 100 g food product.

Dietary Supplements: The term dietary supplement is known in the field and describes a product taken orally that contains one or more ingredients (such as vitamins, minerals, trace elements, fatty acids, amino acids) that are intended to supplement one's diet and are not considered food. Accordingly the term includes tablet formulations, effervescent tablet formulations, powder formulations, as well as gel and liquid formulations. Nutritional doses for the minerals discussed above are known; a typical nutritional dose of iron is 5-30 mg/day; a typical nutrition dose for zinc is 5-30 mg/day. The skilled person is in a position to prepare dietary supplements meeting with these criteria. Accordingly, the amount of composite material (b) (as described herein, 1$^{st}$ aspect of the invention) may vary over a broad range and typically amounts to 1-10 mg nutritional mineral (such as nanoparticular iron mineral) per 100 g dietary supplement, preferably 2-6 mg nutritional mineral (such as nanoparticular iron mineral) per 100 g dietary supplement.

Pharmaceutical Compositions: The term pharmaceutical composition in known in the field and describes any composition suitable for the treatment, prevention or delay of progression of a disease in a subject in need thereof. The term particularly includes formulations adapted for oral administration, e.g. in liquid or solid dosage form. Suitable liquid dosage forms include oral solutions/suspensions, such as syrup. Suitable solid dosage forms include tablets, such as coated or un-coated tablets. Pharmaceutical doses for the minerals discussed above are known; a typical nutritional dose of iron is 30-300 mg/day; a typical nutrition dose for zinc is 30-300 mg/day. The skilled person is in a position to prepare pharmaceutical compositions meeting with these criteria.

In pharmaceutical compositions, the metal of composite material (b) may be the only component of the pharmaceutical composition acting as an active ingredient. Alternatively, the pharmaceutical compositions may comprise two or more different metals as defined above, or other active ingredients.

In a third aspect, the invention relates to pharmaceutical applications of compositions described herein. Suitable dosage regimes and modes of administration may be determined by a person skilled in the art.

This aspect of the invention shall be explained in further detail below.

In one embodiment, the invention provides for a composition comprising a composite material as defined herein (1$^{st}$ aspect of the invention) for use as a pharmaceutical. Suitable pharmaceutical compositions are described herein (2$^{nd}$ aspect of the invention). The use as a pharmaceutical includes the therapy, prevention and delay of progression of a diseases or disorder in a subject in need thereof.

In one embodiment, the invention provides for the use of a composite material as defined herein (1$^{st}$ aspect of the invention) for use in the manufacture of a medicament for the treatment of a disease associated with iron deficiency and/or zinc deficiency.

In one embodiment, the invention provides for a composition comprising a composite material as defined herein (1$^{st}$ aspect of the invention) for use in the treatment of a disease associated with iron deficiency. Accordingly, the invention also provides for a method for the treatment, prevention or delay of progression of a disease associated with iron deficiency in a subject in need thereof, said method comprising the step of administering an efficient amount of a composite material as described herein (1$^{st}$ aspect of the invention).

In one embodiment, the invention provides for a composition comprising a composite material as defined herein (1$^{st}$ aspect of the invention) for use in the treatment of a disease associated with zinc deficiency. Accordingly, the invention also provides for a method for the treatment, prevention or delay of progression of a disease associated with zinc deficiency in a subject in need thereof, said method comprising the step of administering an efficient amount of a composite material as described herein (1$^{st}$ aspect of the invention).

The term disease associated with iron deficiency is known an particularly relates to iron deficiency anemia (IDA); the term disease associated with zinc deficiency is also known. Iron and zinc deficiencies are two major health problems, affecting a large part of the population of all ages worldwide, especially in developing countries. It has been estimated that about 2.2 billion people suffer from iron deficiency and 2.5 billion people suffer from zinc deficiency.

A sustainable and cost-effective strategy to reduce IDA is iron fortification of foods, but the most bioavailable fortificants cause adverse organoleptic changes in foods, as discussed in Hurrell (cited above). When iron nanoparticles are added to food matrices, their tendency to oxidize and rapidly aggregate in solution, as discussed in Huber (cited above), severely limits their use in food fortification.

A sustainable and cost-effective strategy to reduce zinc deficiency is zinc fortification of foods, but currently-available zinc compounds have low bioavailability and often cause sensory changes in foods. Zinc compounds also have a tendency to aggregate in solutions, which limits their use in food fortification.

To further illustrate the invention, the following examples are provided. These examples are provided with no intend to limit the scope of the invention.

EXAMPLE 1: FE-FIBBLG

1. Synthesis & Characterization

These hybrids were prepared in-situ (FIG. 1ab) according to Amar-Yuli et al. (*Soft Matter* 7, 3348-3357 (2011)). Fe (III) ions strongly bind onto premade 2 wt % fibrils at pH 2. Nanosized iron nanoparticles were thus nucleated on the surface of fibrils by adding sodium borohydride. Transmission electron microscopy (TEM) gives insight into the morphology of these hybrids before and after nanoparticle composition. Compared to the typical morphology of BLG fibrils (FIG. 1a), small (5-20 nm in diameter), spherical, nanoparticles were found to decorate the surface of the fibrils (FIG. 1b). For powder form of the material, the liquid sample was freeze dried.

2. Fe-fibBLG—In Vitro Studies

Acidic dissolution and enzymatic hydrolysis on the material were performed separately.

For acidic dissolution, HCl was added to obtain pH=1.2 and the mixture was stirred for 20 min. at RT. It was found that the iron particles are no longer observed but only the fibrils remained after acidic dissolution (FIG. 1c top).

Similarly, enzymatic hydrolysis was performed on the hybrid material. BLG fibrils were hydrolyzed by pepsin at concentration 2 mg/ml with additional 150 mM NaCl, shaken at 50 rpm at 37° C. into short peptides. The iron nanoparticles agglomerated, together with protein residues, thereby forming large clumps in one hour as shown in FIG. 1c bottom. This result indicates that enzymatic hydrolysis of fibrils is slower compared to the fast acidic dissolution of iron nanoparticles. This difference in digestion kinetics allows the delivery of iron ions prior to the digestion of fibrils at low pH conditions in the stomach, hence avoiding iron-particle aggregation, yet allowing the digestion of both the organic and inorganic phases via a synergistic acidic-enzymatic digestion.

3. Fe-fibBLG—In Vivo Studies 3.1 Study design: For 24-25 days 73 rats were made iron deficient (depletion). Over 15 days, 60 rats were fed 3 iron sources incorporated in the pellet diets with 10 or 20 ppm iron (repletion). Over the entire study, 13 and 3 rats received iron deficient (3.9 ppm) and sufficient (35 ppm) diets, respectively.

3.2 The relative bioavailability (RBV) to FeSO$_4$ of inventive composites Fe-FibBLG in solid form was investigated in-vivo using the hemoglobin repletion bioassay in rats. Fe nanoparticles (Fe-Nano) synthesized with the same method but without BLG fibrils were used for comparison. Fe-Nano has similar iron composition as Fe-FibBLG. Fe-FibBLG and Fe-Nano in powder form showed RBVs of 90% and 95%, respectively (FIG. 2a). High bioavailability of the compounds in liquid form was confirmed by a stable isotope study, where erythrocyte incorporation of stable isotopes after gavage administration of $^{57}$Fe-FibBLG (RBV 99%) and $^{58}$Fe-Nano (RBV 96%) was not significantly different from $^{54}$FeSO$_4$. However, when added to liquids (pH 7), Fe-Nano forms a dark yellow turbid solution with flocculated agglomerates that tend to precipitate, whereas Fe-FibBLG forms a stable transparent dispersion, similar to the freshly made one at pH 3.

The high RBV of Fe-FibBLG combined with excellent colloidal stability show that the inventive composite material is a versatile and easy way to fortify iron in liquid matrices.

3.3 Sensory performance of the inventive composites in both powder and liquid forms was further analyzed by the color change in selected food matrices. FeSO$_4$ and iron pyrophosphate (FePP) were used as positive and negative standards, respectively. Selected food matrices were fortified with iron compounds in solid form at concentrations of 2.5 mg iron/100 g and color change was determined by $\Delta$E (FIG. 2b), results are shown in FIG. 2b. FePP showed the least color change because of its low water solubility and tendency to precipitate, which indicates poor absorption. FeSO$_4$, Fe-FibBLG showed significantly less color changes than FeSO$_4$ in most of the matrices, and for chocolate milk this change was below the detection limit of 5 $\Delta E^*_{ab}$.

3.4 Stability in liquid matrices: The increase in turbidity after fortifying fish sauce with 25 mg iron/100 mL and a storage time of 1 month at ambient conditions was evaluated.

The results show that Fe-FibBLG causes significant lower turbidity than FeSO$_4$ (FIG. 2c). These results taken together demonstrate that Fe-FibBLG is a promising carrier and delivery system for nanosized iron, as bioavailable as FeSO$_4$ but with improved sensory performance, and colloidally more stable than standard forms of nanosized iron.

4. Conclusion

The Fe-fibBLG, available in both powder and liquid forms, was shown to have excellent physical stability, chemical properties and to undergo fast acid dissolution and enzymatic digestion, as demonstrated in-vitro. Fe-fibBLG has a bioavailability equivalent to ferrous sulfate in Hb repletion and stable isotope studies in rats, but with less organoleptic changes in foods and without any tissue accumulation. Additionally, its total iron content of 7.0±0.9% in the powder form (corresponding to ~23.9% weight of BLG), is comparable with current available iron fortificants. Its reducing-antioxidant effects, stability in aqueous dispersion, improved sensory performance and high bioavailability, combined with its low cost, demonstrate that nanoparticulate iron compounds—amyloid fibril composite materials are suitable iron fortificants in both solid and liquid foods, dietary supplements and pharmaceutical compositions.

EXAMPLE 2: ZN-FIBBLG

1. Synthesis & Characterization

In analogy to example 1, a solution of 2 wt % BLG fibrils at pH 2 was mixed with $ZnCl_2$. Zinc ions that bound to BLG fibrils were then chemically reduced by $NaBH_4$ to nucleate the zinc nanoparticles (mostly metallic zinc core with ZnO shell) in situ on the fibrils, thus obtained Zn-fibBLG. For powder form of the material, the liquid samples were first centrifuged through a membrane with a pore size of 10 kDa to remove excess mineral compounds, and then freeze dried.

2. Conclusion

The experiment clearly demonstrates that a wide variety of nanoparticulate nutritional mineral compounds may be employed according to this invention.

EXAMPLE 3: FE-FIBLYSOZYME

1. Synthesis & Characterization in analogy to example 1, a solution of 2 wt % Lysozyme fibrils (obtained from purified lysozyme which was extracted from egg white) at pH 2 was mixed with $FeCl_3$. Iron ions that bound to BLG fibrils were then chemically reduced by $NaBH_4$ to nucleate the oxidic iron nanoparticles in situ on the fibrils, thus obtained Fe-fibLysozyme. For powder form of the material, the liquid sample was freeze dried.

2. Conclusion

The experiment clearly demonstrates that a wide variety of amyloid fibrils may be employed according to this invention.

The invention claimed is:

1. A composition selected from the group consisting of food products and dietary supplements, said composition comprising a composite material comprising (a) amyloid fibrils and (b) one or more nanoparticulate nutritional minerals located on the surface of said amyloid fibrils.

2. The composition according to claim 1, where the amyloid fibrils (a)
  are selected from fibrils being ≤10 nm in diameter and ≥1 μm in length; and/or
  have electrophoretic mobilities of an order of 1-4 μm·cm/V·s at pH 4; and/or
  are obtained from milk, egg, soy, serum, mushrooms, oat, and/or insects; and/or
  are selected from food grade products.

3. The composition according to claim 1, where the amyloid fibrils (a) are obtained from globular proteins selected from the group consisting of whey, beta-lactoglobulin, lysozyme, Bovine serum albumin, soy proteins, ovalbumin and oat.

4. The composition according to claim 1, where the amyloid fibrils (a) are obtained from oat.

5. The composition according to claim 4, where said minerals (b)
  have a particle size within a range of 5-20 nm; and/or
  comprise at least 50 mol % Fe (II) in respect to the total amount of iron.

6. The composition according to claim 5, where a ratio of component (a) to component (b) is in within a range of 20/1 to 1/1 (w/w).

7. The composition according to claim 1, where said minerals (b) are selected from the group consisting of iron salts, iron oxides, and iron hydroxides.

8. The composition according to claim 1, where a ratio of component (a) to component (b) is in within a range of 20/1 to 1/1 (w/w).

9. The composition according to claim 1, wherein the composite material is present as:
  a dry material;
  a gel;
  an aqueous solution at pH 2-4; or
  an aqueous solution at pH 6-10.

10. The composition according to claim 1, wherein the composite material is present as:
  a freeze-dried material; or
  an aqueous gel comprising NaCl as an additional component.

11. The composition of claim 1, which is
  the food product comprising 1-10 mg nutritional mineral per 100 g food product; or
  the dietary supplement comprising 1-10 mg nutritional mineral per 100 g dietary supplement.

12. The composition of claim 11, wherein the dietary supplement is-selected from the group consisting of
  a powder formulation;
  an effervescent tablet;
  a gel formulation; and
  a liquid formulation.

13. The composition of claim 11, wherein the food product is selected from the group consisting of
  a drink;
  a snack product; and
  a sauce formulation.

14. The composition of claim 13, wherein the food product is selected from the group consisting of
  a flavoured milk product;
  a flavoured yoghurt product;
  a cereal based product
  a fruit based product;
  a fish sauce formulation; and
  a soy sauce formulation.

* * * * *